US011583263B2

(12) United States Patent
Buttermann et al.

(10) Patent No.: US 11,583,263 B2
(45) Date of Patent: Feb. 21, 2023

(54) DILATOR ASSEMBLY

(71) Applicant: Dynamic Spine LLC, Mahtomedi, MN (US)

(72) Inventors: Glenn R. Buttermann, Mahtomedi, MN (US); Frank Ferris, Mahtomedi, MN (US)

(73) Assignee: DYNAMIC SPINE LLC, Mahtomedi, MN (US)

( * ) Notice: Subject to any disclaimer, the term of this patent is extended or adjusted under 35 U.S.C. 154(b) by 0 days.

(21) Appl. No.: 17/406,665

(22) Filed: Aug. 19, 2021

(65) Prior Publication Data
US 2022/0054121 A1    Feb. 24, 2022

Related U.S. Application Data

(60) Provisional application No. 63/067,652, filed on Aug. 19, 2020.

(51) Int. Cl.
*A61B 17/02*    (2006.01)
*A61M 29/00*    (2006.01)

(52) U.S. Cl.
CPC .. *A61B 17/0206* (2013.01); *A61B 2017/0256* (2013.01); *A61M 29/00* (2013.01)

(58) Field of Classification Search
CPC .............. A61M 29/00; A61B 17/0218; A61B 17/0206; A61B 17/025; A61B 2017/0256; A61B 17/3423; A61B 17/3439
See application file for complete search history.

(56) References Cited

U.S. PATENT DOCUMENTS

2009/0024158 A1\*    1/2009    Viker ................. A61B 17/0218
606/201

\* cited by examiner

*Primary Examiner* — Eduardo C Robert
*Assistant Examiner* — Christina Negrellirodriguez
(74) *Attorney, Agent, or Firm* — Foley & Lardner LLP

(57) ABSTRACT

A dilator assembly includes a blade, a tubular member defining a passage extending along a longitudinal axis, a guide needle received within the passage, a first link having a first end pivotally coupled to the tubular member and a second end pivotally coupled to the blade, and a second link having a first end pivotally coupled to the tubular member and a second end pivotally coupled to the blade.

20 Claims, 14 Drawing Sheets

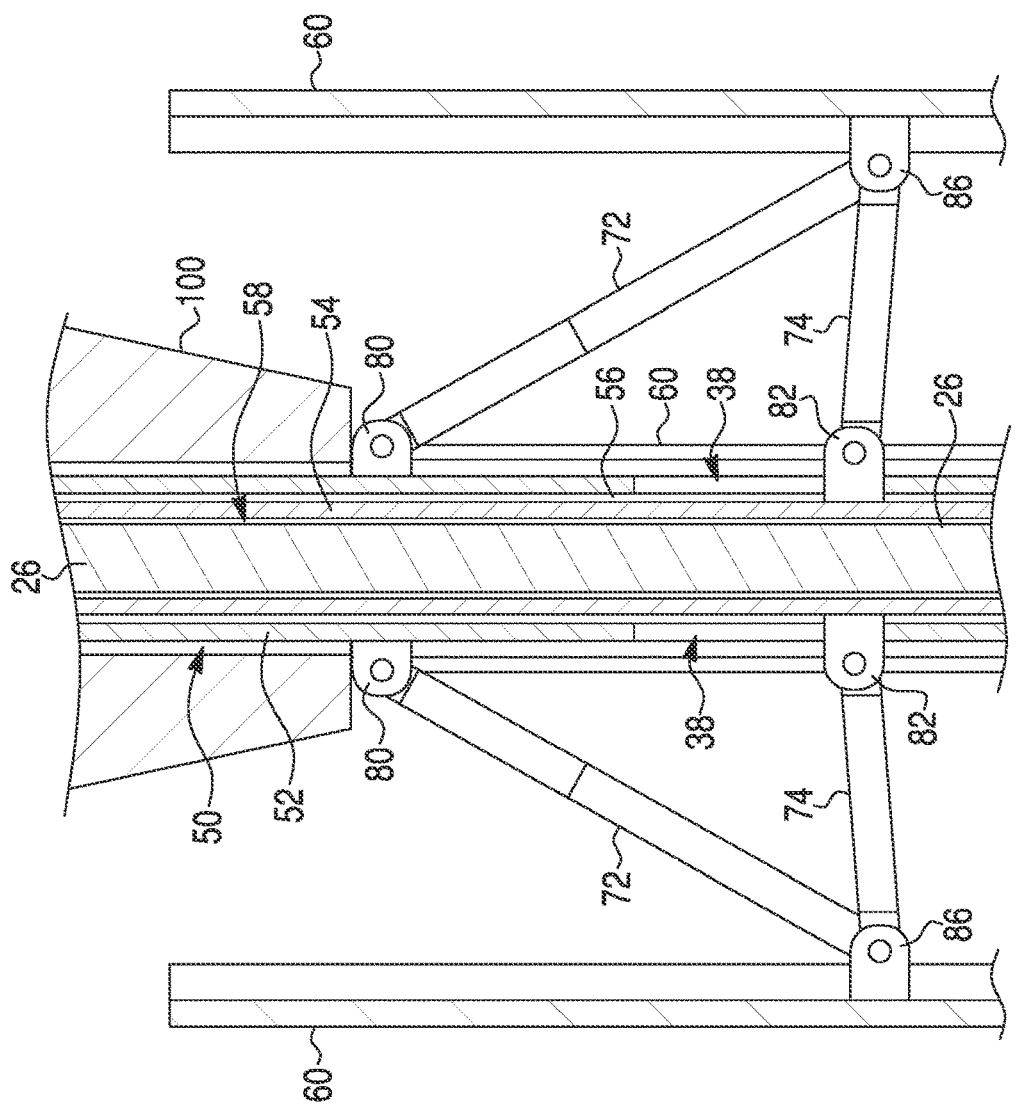
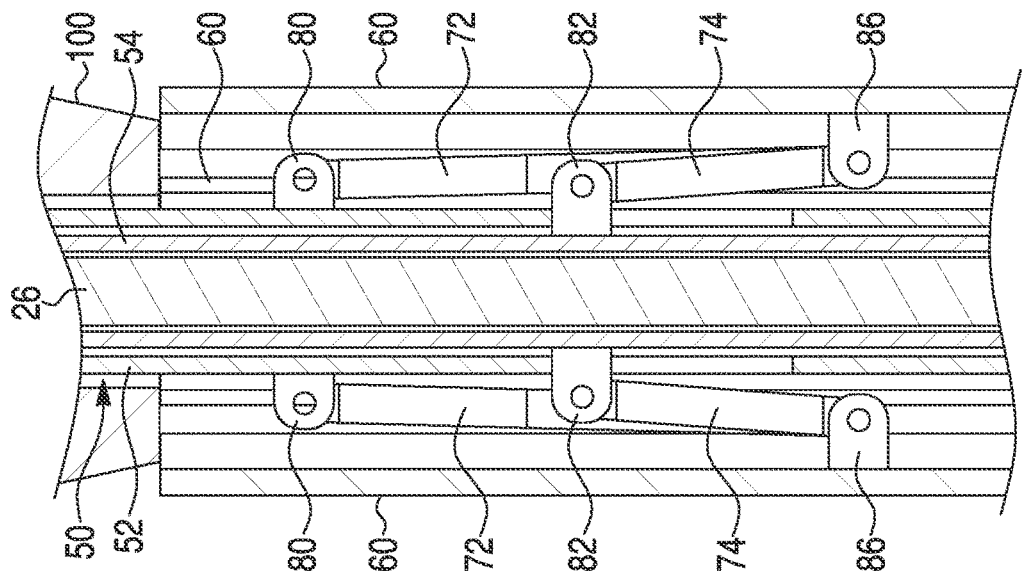

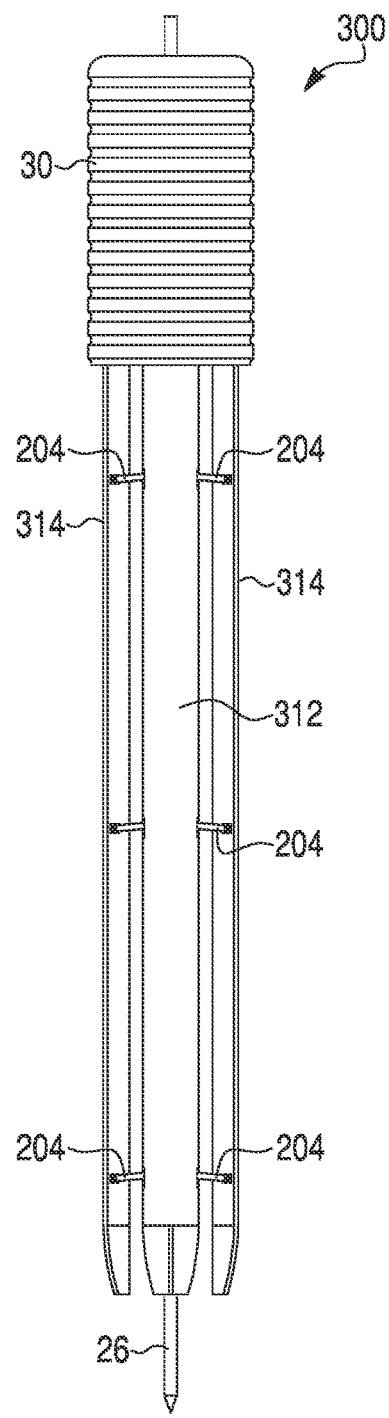 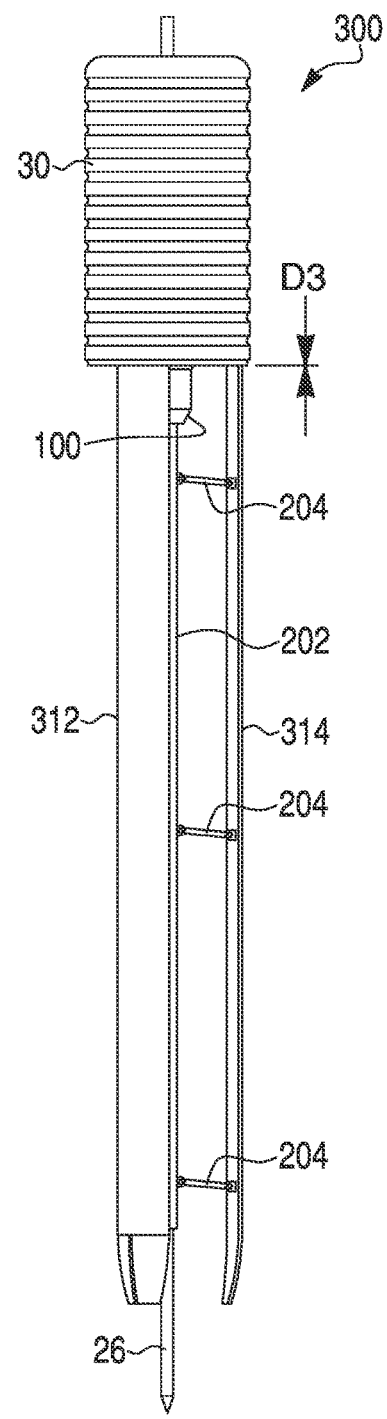
FIG. 14A
FIG. 14B

DILATOR ASSEMBLY

CROSS-REFERENCE TO RELATED PATENT APPLICATION

This application claims the benefit of and priority to U.S. Provisional Application No. 63/067,652, filed on Aug. 19, 2020, the entire disclosure of which is hereby incorporated by reference herein.

BACKGROUND

The present disclosure relates generally to the field of surgical instruments. More specifically, the present disclosure relates to dilators for separating soft tissue.

SUMMARY

At least one embodiment relates to a dilator assembly including a blade, a tubular member defining a passage extending along a longitudinal axis, a guide needle received within the passage, a first link having a first end pivotally coupled to the tubular member and a second end pivotally coupled to the blade, and a second link having a first end pivotally coupled to the tubular member and a second end pivotally coupled to the blade.

Another embodiment relates to a dilator assembly including a blade, a first member extending along a longitudinal axis, a second member slidably coupled to the first member and configured to translate relative to the first member along the longitudinal axis, a first link having a first end pivotally coupled to the first member and a second end pivotally coupled to the blade, and a second link having a first end pivotally coupled to the second member and a second end pivotally coupled to the blade. The first link and the second link are configured to move the blade away from the first member and the second member in response to longitudinal movement of the second member relative to the first member.

Another embodiment relates to a surgical method including inserting a guide needle into a disc of a spine, moving a dilator assembly along a length of the guide needle, the dilator assembly including a tubular member that receives the guide needle and a plurality of blades coupled to the tubular member by a plurality of links, forcing the dilator assembly toward the spine such that the blades of the dilator assembly penetrate soft tissue adjacent the spine, and expanding the dilator assembly such that the blades move radially outward from the tubular member, forming a cavity in the soft tissue.

This summary is illustrative only and is not intended to be in any way limiting. Other aspects, inventive features, and advantages of the devices or processes described herein will become apparent in the detailed description set forth herein, taken in conjunction with the accompanying figures, wherein like reference numerals refer to like elements.

BRIEF DESCRIPTION OF THE DRAWINGS

FIG. 12A is a close-up view of a portion of the dilator assembly of FIG. 1 in the contracted position.

FIG. 12B is a close-up view of a portion of the dilator assembly of FIG. 1 in the expanded position.

FIG. 14A is a side view of the dilator assembly of FIG. 13A in the expanded position.

FIG. 14B is a side view of the dilator assembly of FIG. 14A, rotated approximately 15°.

DETAILED DESCRIPTION

Before turning to the figures, which illustrate certain exemplary embodiments in detail, it should be understood that the present disclosure is not limited to the details or methodology set forth in the description or illustrated in the figures. It should also be understood that the terminology used herein is for the purpose of description only and should not be regarded as limiting.

Referring generally to the figures, various implementations disclosed herein relate to a dilator assembly that is movable between a contracted position (e.g., a contracted configuration) and an expanded position (e.g., an expanded configuration) to create a cavity in soft tissue.

Figure 1:
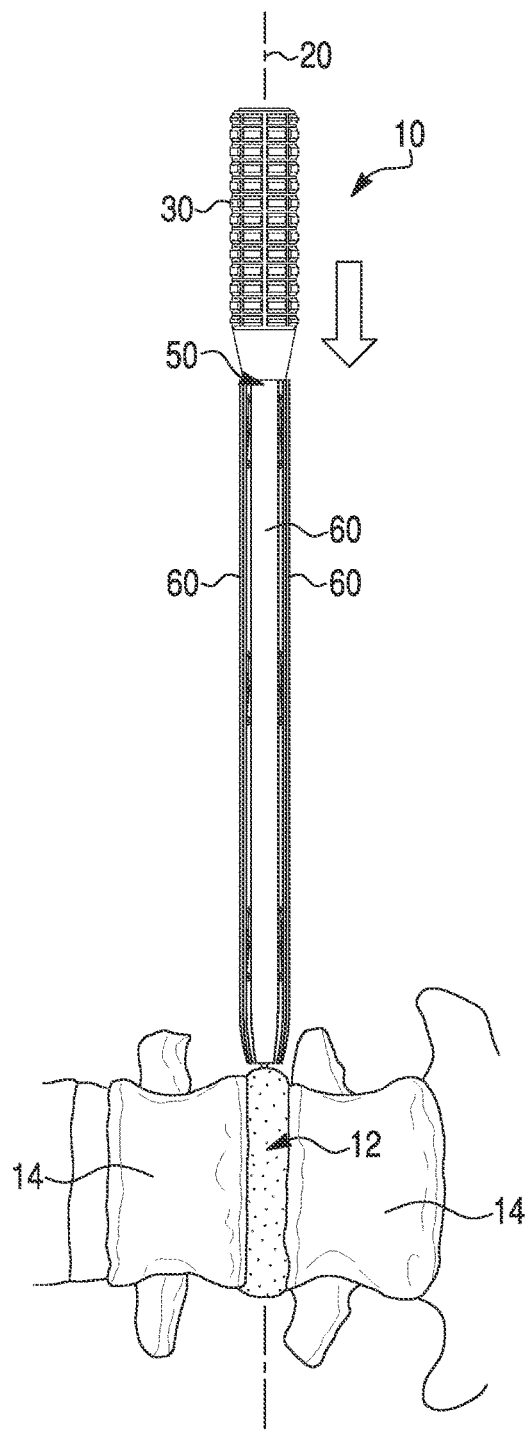
FIG. 1 is a side view of a dilator assembly according to one embodiment in a contracted position being used with a spine.
Figure 2:
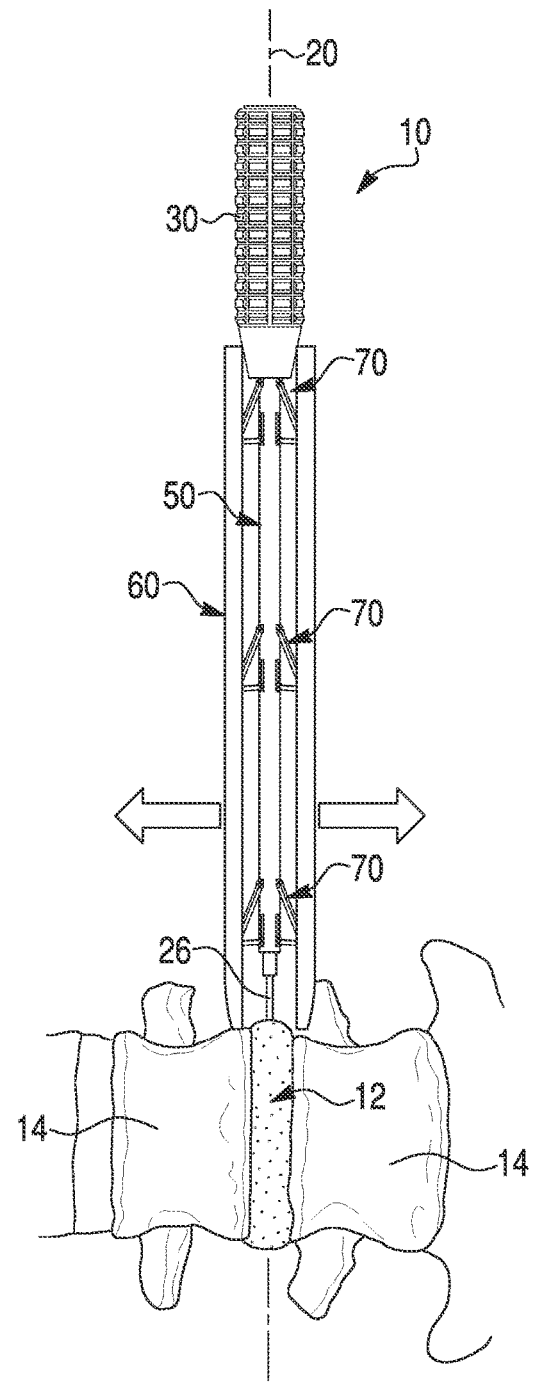
FIG. 2 is a side view of the dilator assembly of FIG. 1 in an expanded position being used with the spine.
Figure 3A:
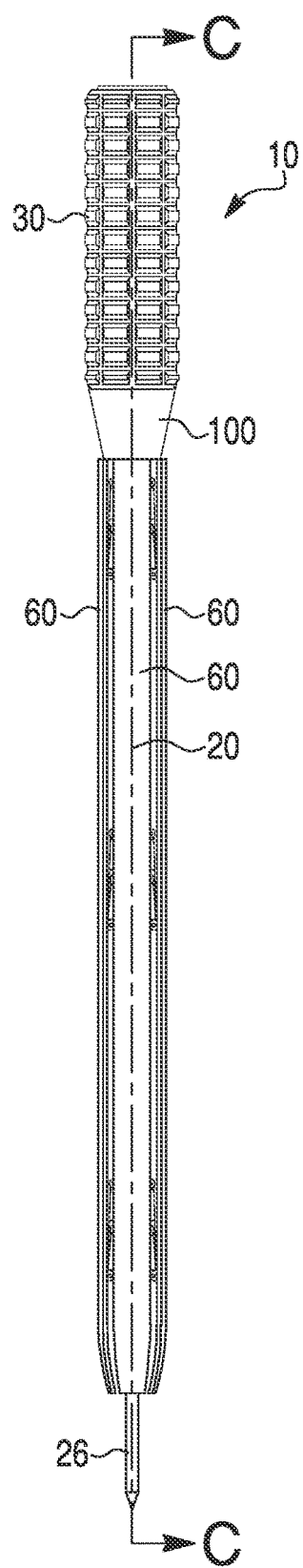
FIG. 3A is a side view of the dilator assembly of FIG. 1 in the contracted position.
Figure 3B:
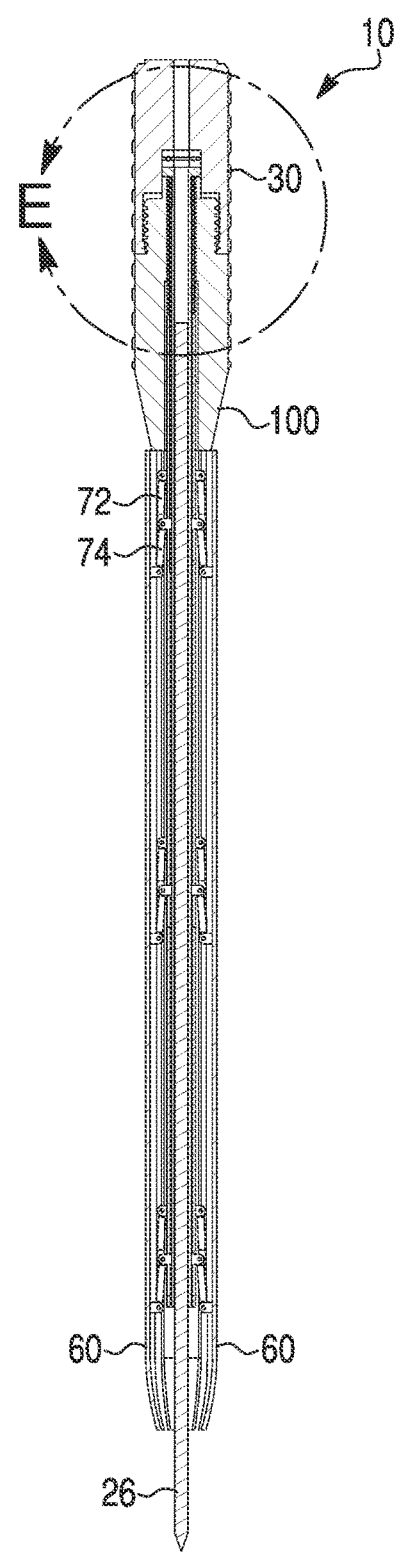
FIG. 3B is a cross-sectional view through Section C-C of FIG. 3A.
Figure 3C:
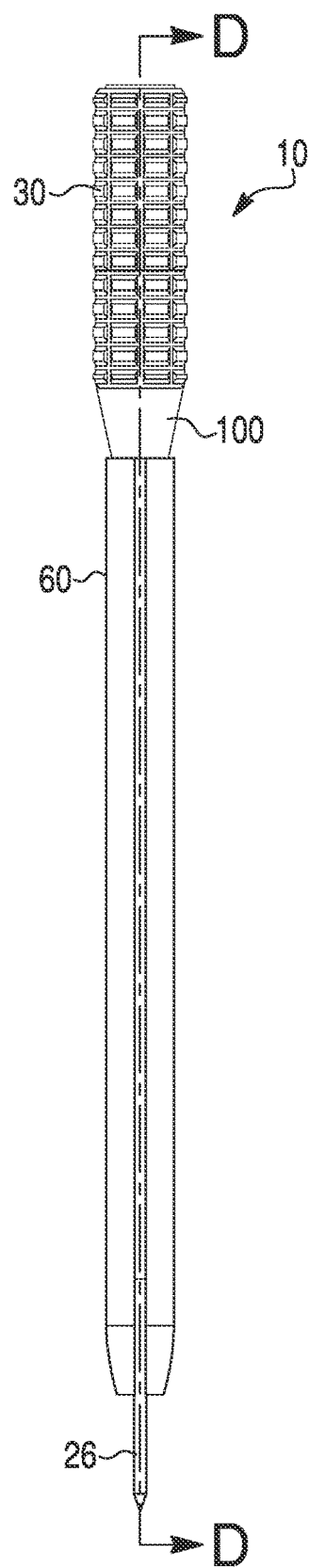
FIG. 3C is a side view of the dilator assembly of FIG. 3A turned approximately 45°.
Figure 3D:
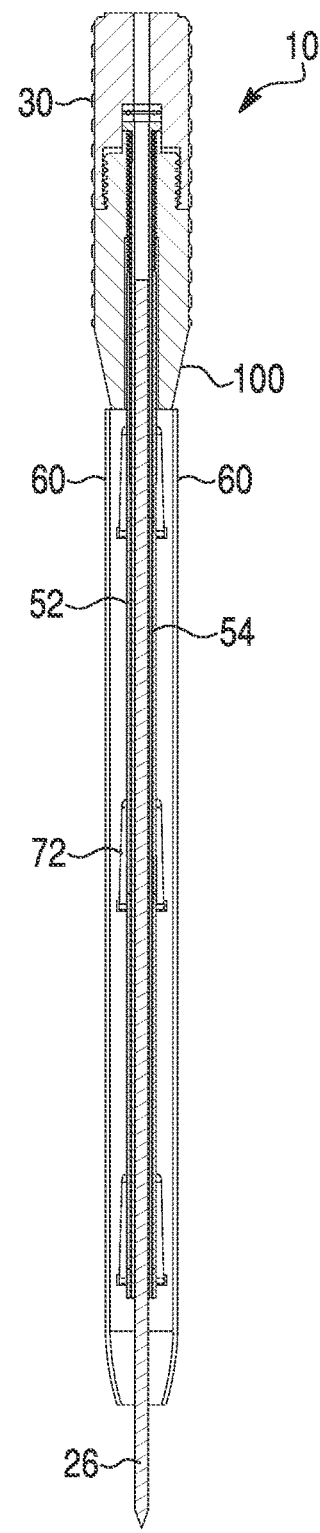
FIG. 3D is a cross-sectional view through Section D-D of FIG. 3C.
Figure 4A:
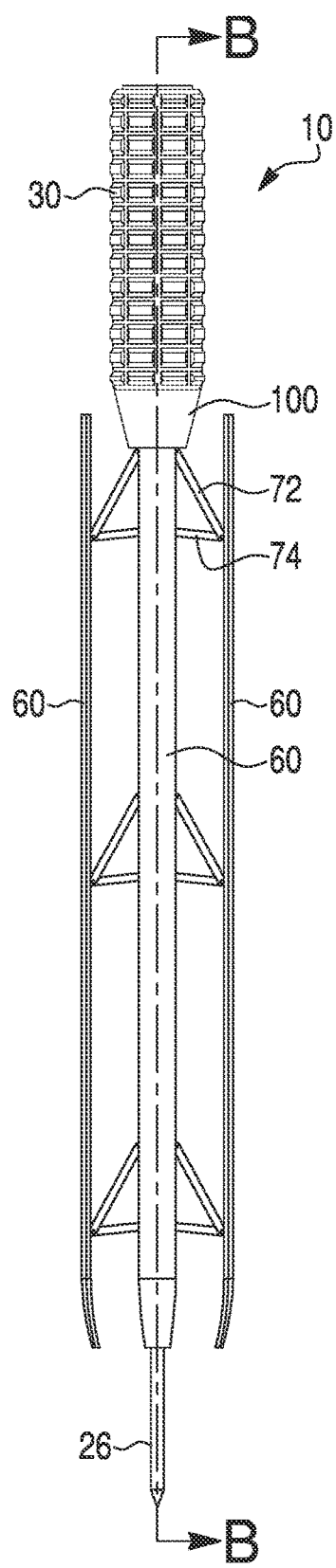
FIG. 4A is a side view of the dilator assembly of FIG. 1 in the expanded position.
Figure 4B:
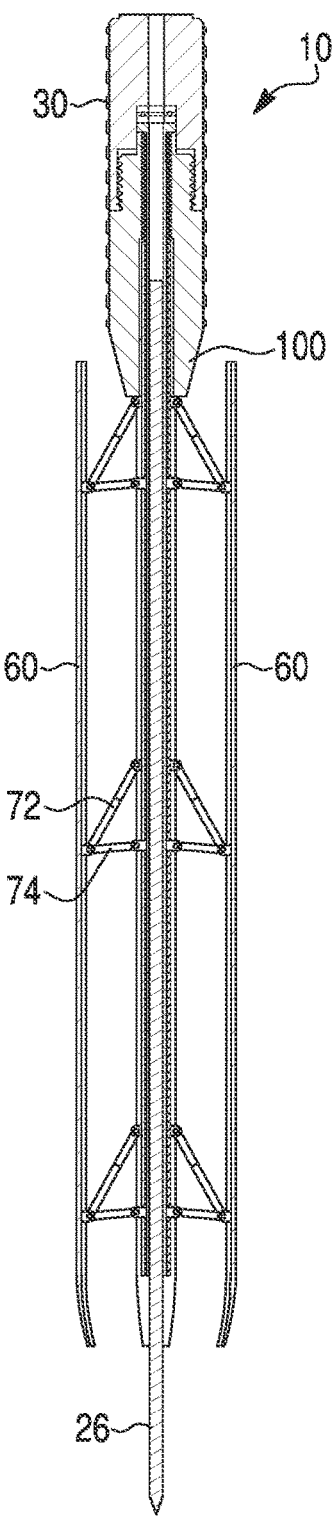
FIG. 4B is a cross-sectional view through Section B-B of FIG. 4A.
Figure 4C:
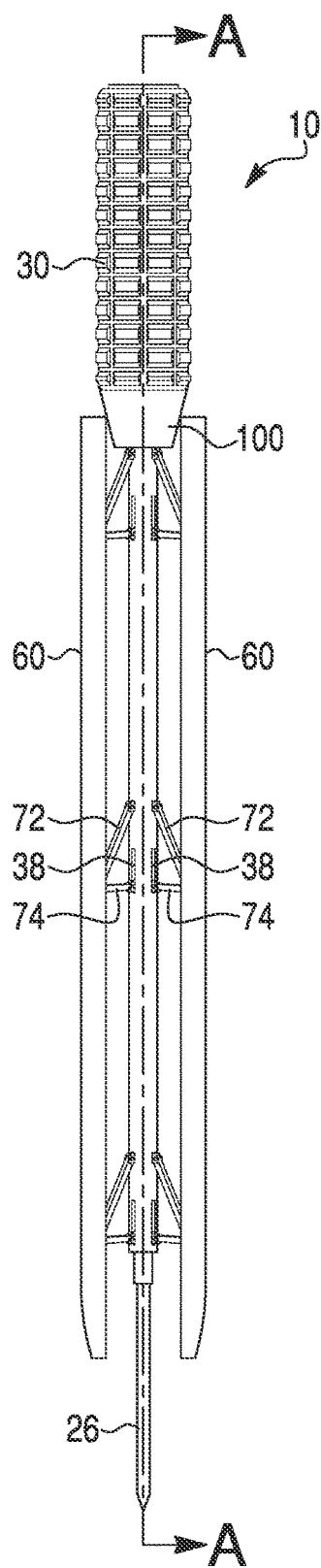
FIG. 4C is a side view of the dilator assembly of FIG. 4A turned approximately 45°.
Figure 4D:
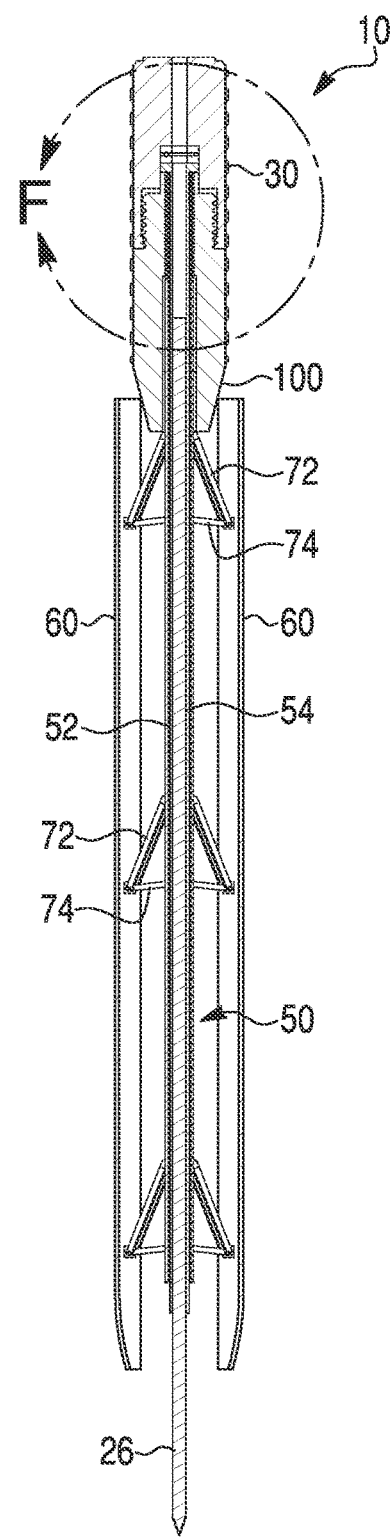
FIG. 4D is a cross-sectional view through Section A-A of FIG. 4C.

As shown in FIGS. 1-2, a soft-tissue dilator assembly, shown as dilator assembly 10, is configured to be used with a spine, in particular with a disc 12 and adjacent vertebral bodies 14 along the lumbar spine (e.g., of a human). By moving and expanding from the contracted position to the expanded position, the dilator assembly 10 creates a tubular cavity in soft tissue adjacent the spine. A surgeon can then access the disc 12 through the formed or created cavity, place other retractors (such as deep retractors) or instruments in the cavity and/or the disc, and/or perform surgery in the deep tissues via the cavity.

Figure 7:
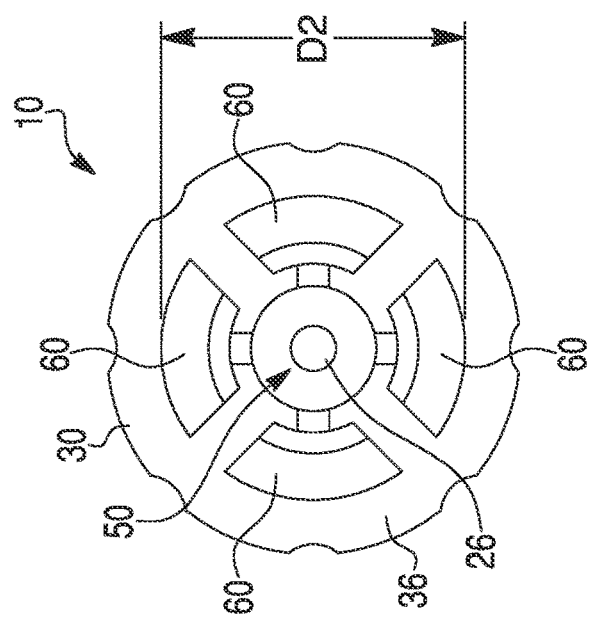
FIG. 7 is a bottom view of the dilator assembly of FIG. 1 in the contracted position.

As shown in FIG. 2, the dilator assembly 10 comprises a guide pin 26 (e.g., a locator needle, a guide needle, etc.), a handle 30 (e.g., an interface, a knob, etc.), an inner tube assembly 50 (e.g., an inner tube, a telescoping assembly, etc.), at least one (preferably a plurality of) blades 60 (e.g., leaves, blades, separators, outer members, fingers, plates, etc.), and at least one (preferably a plurality of) links 70 (e.g., spokes, links, levers, bars, etc.). The dilator assembly 10 may have, for example, four blades 60 that are radially spaced apart from each other about and radially surround the inner tube assembly 50. Specifically, as shown in FIGS. 7 and 9, the blades 60 are each radially offset from one another by approximately 90 degrees. The inner tube assembly 50 is positioned radially within and movably attached to the handle 30 and an inner area defined by the blades 60. In particular, a top end of the inner tube assembly 50 is attached to the handle 30, and a bottom end of the inner tube assembly 50 is positioned within an inner area defined by the blades 60. Accordingly, the bottom ends of the blades 60 extend axially beyond the bottom end of the inner tube assembly 50. As shown in FIGS. 1-2, when in use, the bottom ends of the blades 60 directly abut the soft tissue, and the bottom end of the inner tube assembly 50 is axially spaced apart from the soft tissue. As shown, the dilator assembly 10 extends along and is centered about a longitudinal axis, shown as central axis 20. Specifically, the guide pin 26, the handle 30, and the inner tube assembly 50 are centered about the central axis 20. The blades 60 are each equally spaced from the central axis 20.

Figure 8:
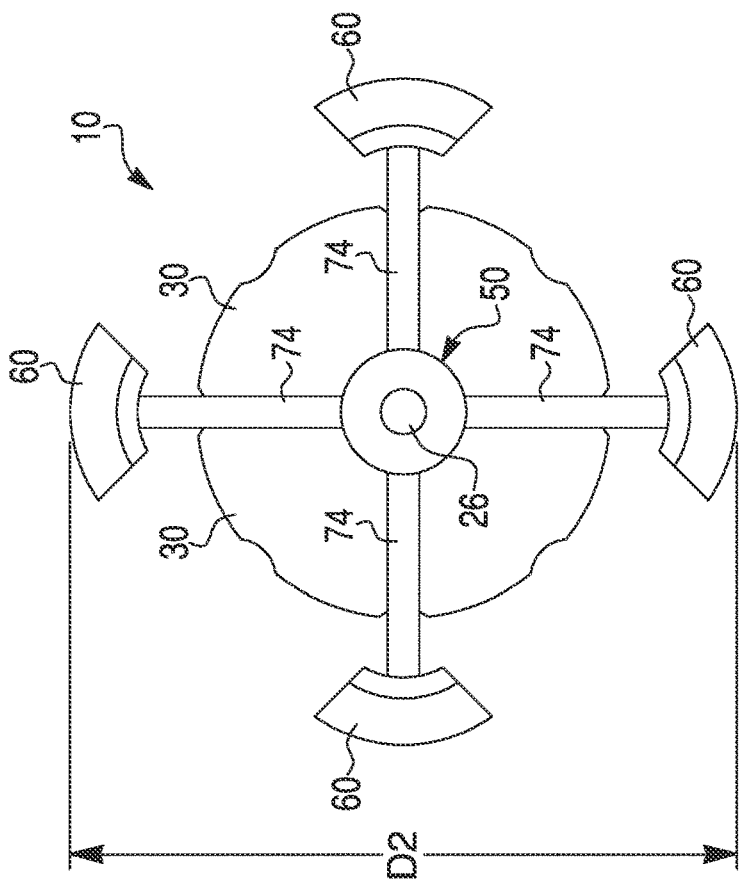
FIG. 8 is a bottom view of the dilator assembly of FIG. 1 in the expanded position.
Figure 15A:
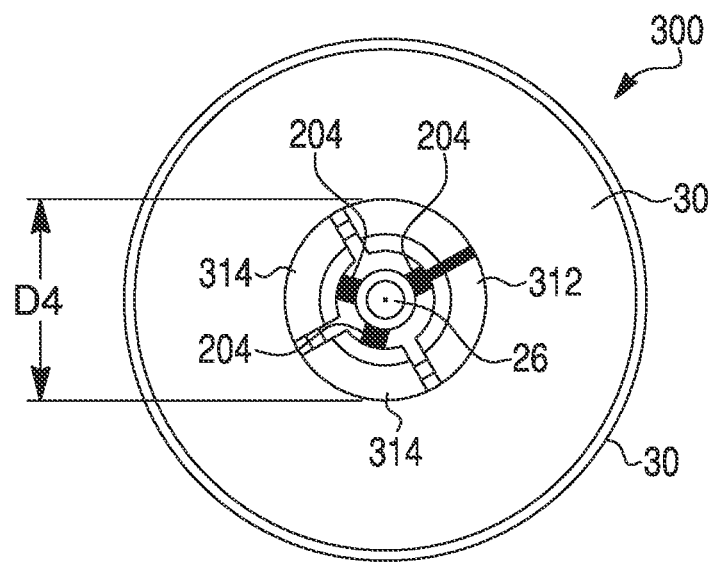
FIG. 15A is a bottom view of the dilator assembly of FIG. 13A in the contracted position.
Figure 15B:
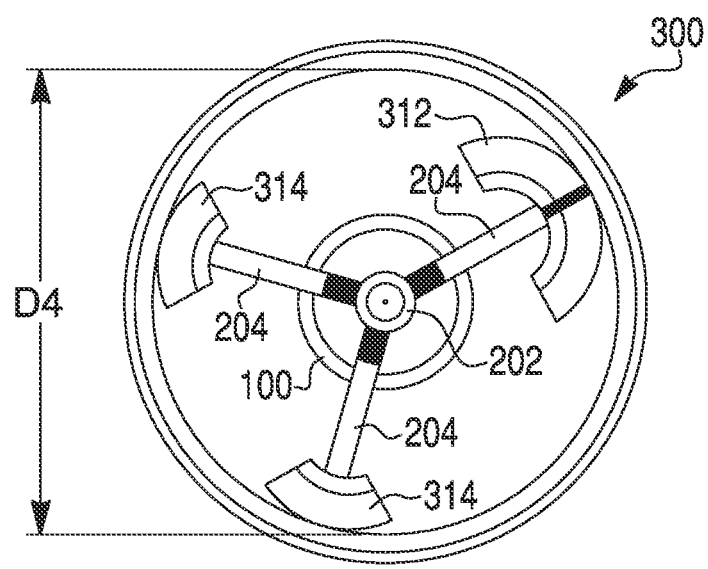
FIG. 15B is a bottom view of the dilator assembly of FIG. 13A in the expanded position.

The blades 60 may have the same size and shape as each other (as shown in FIGS. 7-8) or may have different sizes and shapes (as shown in FIGS. 15A-15B). Additionally, the dilator assembly 10 may be symmetric or asymmetric (e.g., radially symmetric, symmetric about a plane extending along the center axis of the dilator assembly).

According to various embodiments, the inner tube assembly 50 is a double inner tube assembly 50 that comprises two sliding tubes positioned around the guide pin 26: an outer tubular member 52 (e.g., an outermost tube, an outer tube, an outer member, an outer tubular member, etc.) and an inner tubular member 54 (e.g., an innermost tube, an inner tube, an inner member, etc.) that is positioned radially within the outer tubular member 52. As shown in FIGS. 12A-12B, the outer tubular member 52 defines a longitudinal passage 56 that receives the inner tubular member 54. Each end of the longitudinal passage 56 defines an aperture. The inner tubular member 54 defines a longitudinal passage 58 that receives the guide pin 26. Each end of the longitudinal passage 58 defines an aperture. The longitudinal passage 56 and the longitudinal passage 58 are centered about the central axis 20. The outer tubular member 52 and the inner tubular member 54 are axially movable relative to each other (e.g., longitudinally translatable relative to one another, slidably coupled to one another, etc.), thereby allowing the dilator assembly 10 to move between the contracted position and the expanded position, as described further herein. The outer tubular member 52 is threaded to (e.g., in threaded engagement with) the handle 30. The inner tubular member 54 is rotatably coupled to the handle 30.

Each of the blades 60 are attached to the inner tube assembly 50 through the levers or links 70. Accordingly, the links 70 are positioned and extend radially between the inner tube assembly 50 and the blades 60. According to various embodiments, each of the links 70 refers to a pair of links that includes an upper link 72 and a lower link 74. For example, three pairs of links 70 may attach each of the blades 60 to the inner tube assembly 50. The two links 72, 74 in each of the pairs of links 70 may be different lengths and attached at different axial positions along the axial length of the inner tube assembly 50 and attached to similar axial positions along the axial length of the inner surface of the blades 60. Accordingly, the two links in each of the pairs of links 70 may be oriented at different angles relative to each other.

According to various embodiments (see, for example, FIGS. 4B, 9B, 11B, and 12B), each pair of links 70 includes a top or upper link 72 and a bottom or lower link 74 that are both rotatably or hingeably mounted to the inner tube assembly 50 (along an inner end of the links 72, 74 and at approximately the same radial position and two different axial positions) and the same outer leaf B (along an outer end of the links 72, 74 and at approximately the same radial and axial position). As shown in FIGS. 11A-12B, the links 72, 74 rotate and pivot relative to the inner tube assembly 50 and the blades 60 as the dilator assembly moves between the contracted position and the expanded position.

The bottom or lower link 74 refers to the link (of the pair of links 70) that is axially closer to the exposed end of the guide pin 26 and axially further from the handle 30 relative to the upper link 72. The inner end (e.g., a first end portion) of the top or upper link 72 of the pair of links is directly hingeably attached to the outer surface of the outer tubular member 52 of the inner tube assembly 50 at a position above the lower link 74. Specifically, the inner end of the upper link 72 is pivotally coupled to a protrusion 80 of the outer tubular member 52 that extends radially outward from an outer circumference of the outer tubular member 52. The inner end (e.g., a first end portion) of the lower link 74 is directly hingeably attached to the outer surface of the inner tubular member 54 of the inner tube assembly 50 through a slot 38 (see FIG. 12B) formed in the sidewall of the outer tubular member 52. Specifically, the inner tubular member 54 includes a protrusion 82 that extends radially outward from an outer circumference of the inner tubular member 54 and that is received by the slot 38. The inner end of the lower link 74 is pivotally coupled to the protrusion 82. The slot 38 is a passage that extends radially through the outer tubular member 52, outward from the longitudinal passage 56. The slot 38 extends axially (e.g., longitudinally) along a portion of the axial length of the outer tubular member 52 such that the inner end of the lower link 74 can move axially (relative to the outer tubular member 52) along the axial length of the slot 38. Engagement between the walls of the slots 38 and the protrusions 82 may limit (e.g., prevent) rotation of the inner tubular member 54 relative to the outer tubular member 52.

The respective outer ends (e.g., second end portions) of the upper link 72 and the lower link 74 are directly hingeably attached to approximately the same radial and axial position along the inner surface of the blade 60. Specifically, the blade 60 includes a protrusion 86 that extends radially inward from an inner surface of the blade 60. The outer ends of the upper link 72 and the lower link 74 are each pivotally coupled to the protrusion 86. The upper link 72 and the lower link 74 each rotate about a common axis (i.e., about the same axis) that extends through the protrusion 86.

Accordingly, the upper link 72 is angled downwardly toward the inner end of the lower link 74 and between the connection to the inner tube assembly 50 and the connection to the blade 60 (in both the contracted position (at a greater downward angle) and the extended position (at a smaller downward angle)). In the contracted position, the lower link 74 is also angled downwardly toward the lower link 74 and between the connection to the inner tube assembly 50 and the connection to the outer leaf B. In the extended position, however, the lower link 74 extends radially between and approximately perpendicularly to the inner tube assembly 50 and the blade 60 (or optionally at a slight angle). According to various embodiments, the upper link 72 and the lower link 74 may be switched with each other.

As the dilator assembly moves between the contracted position and the extended position, the links 72 and 74 move relative to each other (as the outer tubular member 52 and the inner tubular member 54 also move relative to each other).

Each of the links 70 are rotatably or hingeably fixed to the outer surface of the inner tube assembly 50 (in particular to either the outer surface of the outer tubular member 52 or the outer surface of the inner tubular member 54) and to the inner surface of the blades 60, thereby allowing the blades 60 to move axially and radially relative to the inner tube assembly 50 as the dilator assembly moves between the contracted position and the expanded position. The dilator assembly may utilize and comprise a variety of different springs and/or threads in order to moveably attach the various components together.

The links 70, the inner tube assembly 50, and blades 60 form a series of four bar linkages. Specifically, the outer tubular member 52, the upper links 72, and the blades 60 each form a series of first four bar linkages. The inner tubular member 54, the lower links 74, and the blades 60 each form a series of second four bar linkages. In some embodiments, the four bar linkages maintain a consistent orientation of the blades 60 relative to the central axis 20 throughout the range of motion of the dilator assembly 10. In some such embodiments, the blades 60 extend substantially parallel to the central axis 20 throughout the range of motion of the dilator assembly 10.

FIGS. 3A-3D, 11A, and 12A show the dilator assembly 10 in the closed, collapsed, or contracted position or configuration. In the contracted position, the blades 60 are positioned radially inwardly and closer to the inner tube assembly 50 (relative to the expanded position). The links 70 are each positioned at a relatively small angle relative to the outer surface of the inner tube assembly 50 (e.g., and thus to the central axis 20). The attachment point of each of the links 70 to the outer surface of the inner tube assembly 50 (e.g., the protrusion 80 or the protrusion 82) is axially higher than the attachment point of each of the links 70 to the inner surface of the blades 60 (e.g., the protrusion 86), facilitating outward radial movement of the links 70 as the inner tube assembly 50 moves axially downward (as described further herein).

FIGS. 4A-4D, 11B, and 12B show the dilator assembly 10 in the open, dilated, or expanded position or configuration. In the expanded position, the blades 60 are positioned radially outwardly and further from the inner tube assembly 50 (relative to the contracted position). The links 70 are each positioned at a relatively large angle to the outer surface of the inner tube assembly 50.

FIGS. 5 and 11A and 6 and 11B show the knob or handle 30 of the dilator assembly 10 when the dilator assembly 10 is in the contracted position and the expanded position, respectively. The handle 30 may comprise inner threads (e.g., female threads), and the outer surface of the outer tubular member 52 along the axial top end of the inner tube assembly 50 may include outer threads (e.g., mail threads), where the inner threads and the outer threads are configured to threadably attach to (e.g., engage with) each other. Accordingly, the handle 30 and the outer tubular member 52 of the inner tube assembly 50 may be movably and threadably attached to each other. The top end of the inner tubular member 54 is also positioned within the handle 30 and is movably attached to the handle 30. Specifically, the top end of the inner tubular member 54 is rotatably coupled to the inner tubular member 54 such that axial movement of the handle 30 relative to the inner tubular member 54 is limited. In some embodiments, the handle 30 rotates to move the outer tubular member 52 relative to the inner tubular member 54, thereby repositioning the dilator assembly 10 between the contracted position and the expanded position. As shown, the distance D1 between the axial top end of the outer tubular member 52 of the inner tube assembly 50 and the axial top end of the inner threads of the handle 30 is larger in the contracted position (i.e., FIG. 5) and smaller in the expanded position (i.e., FIG. 6). For example, the distance D1 may be approximately 6.6 millimeters (mm) in the contracted position and 0.0 mm in the expanded position.

Figure 5:
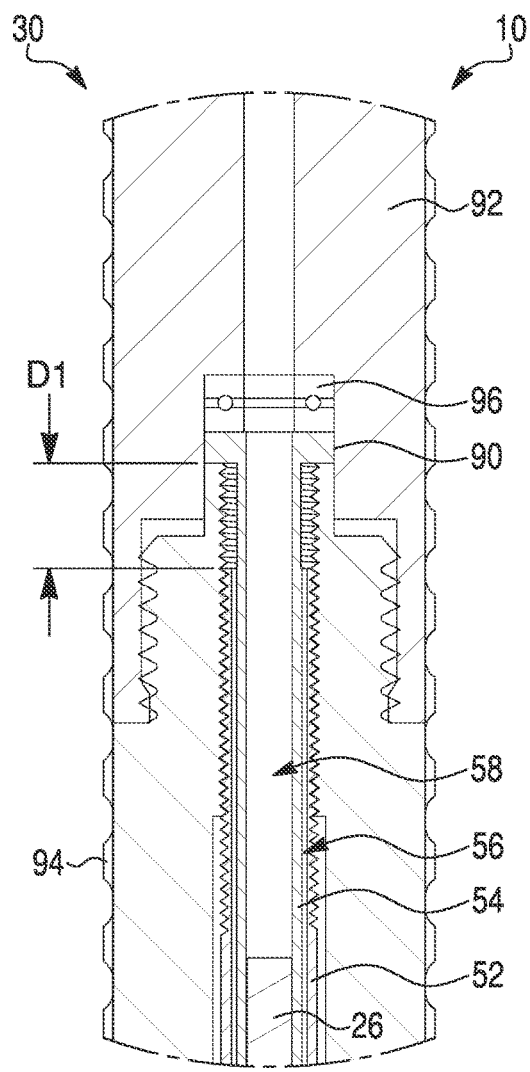
FIG. 5 is a detail view of Section E of FIG. 3B.
Figure 6:
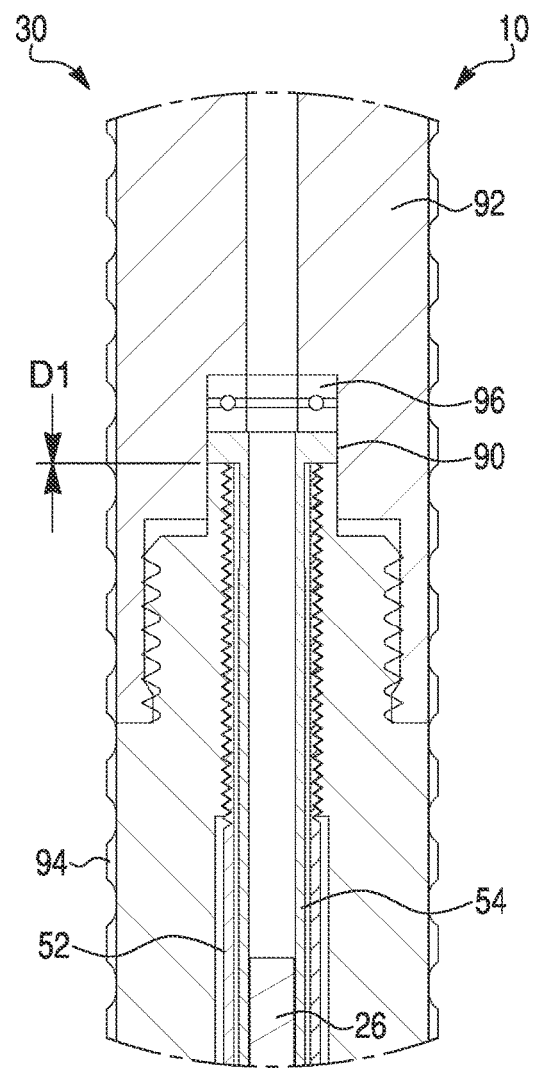
FIG. 6 is a detail view of Section F of FIG. 4D.

In the embodiment of FIGS. 5-6, the top end of the inner tubular member 54 is captured within the handle 30 to limit axial movement of the inner tubular member 54 relative to the handle 30. Specifically, the top end of the inner tubular member 54 includes a radial protrusion or annular protrusion, shown as shoulder 90. The handle 30 includes a first portion, shown as top portion 92, and a second portion, shown as bottom portion 94. The top portion 92 and the bottom portion 94 are in threaded engagement with one another such that the top portion 92 and the bottom portion 94 are selectively coupled to one another. The bottom portion 94 defines a passage that receives the inner tube assembly 50. The shoulder 90 is positioned between the top portion 92 and the bottom portion 94 such that axial movement of the shoulder 90 relative to the handle 30 is limited (e.g., prevented). In some embodiments, a bearing or bushing, shown as thrust bearing 96, is positioned between the shoulder 90 and the top portion 92. The thrust bearing 96 may facilitate rotation of the handle 30 relative to the inner tubular member 54.

However, according to another embodiment, the handle 30 may not include these internal threads, and the inner tube assembly 50 may not include these outer threads. In such an embodiment, the axial top end of the inner tube assembly 50 may be press fit into the handle 30, and the handle 30 may move the dilator assembly between the contracted position and the expanded position by simply pushing or pulling the inner tube assembly 50 axially (and providing a resulting axial force to the inner tube assembly 50).

Figure 9A:
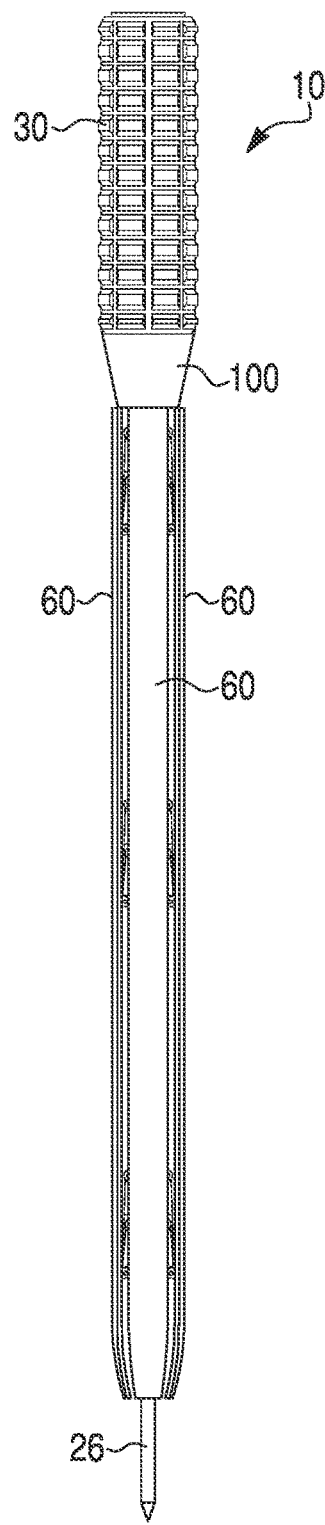
FIG. 9A is a side view of the dilator assembly of FIG. 1 in the contracted position.
Figure 9B:
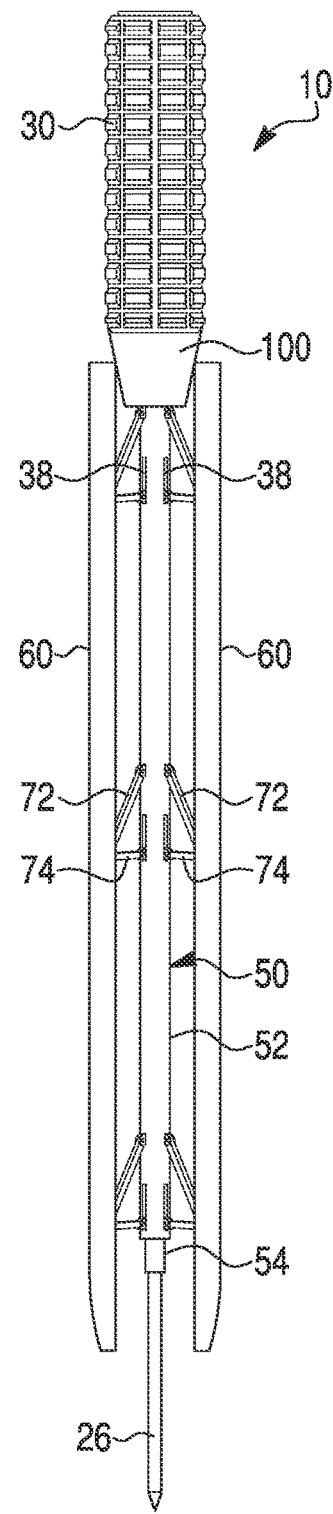
FIG. 9B is a side view of the dilator assembly of FIG. 9A in an expanded position and turned approximately 45°.

Referring to FIGS. 9A-9B, the handle 30 includes an engagement portion, shown as tapered portion 100. The tapered portion 100 makes up the bottommost portion of the handle 30 (e.g., the end of the handle 30 closest to the exposed end of the guide pin 26). The tapered portion 100 gradually decreases in diameter as the tapered portion 100 extends toward the exposed end of the guide pin 26). The tapered portion 100 may be frustoconical or have another tapered profile. As the dilator assembly 10 moves toward the expanded position, the outer tubular member 52 moves toward the handle 30, drawing the blades 60 toward the handle 30. This movement causes the top ends of the blades 60 to engage the tapered portion 100. The tapered surface of the tapered portion 100 forces the blades 60 radially outward, assisting the forces of the links 70 in expanding the blades 60. The tapered portion 100 may engage the blades 60 at any point throughout the movement of the dilator assembly 10 between the contracted position and the expanded position (e.g., throughout only a portion of the range of motion, throughout the entire range of motion, etc.).

FIGS. 7-8 show the bottom of the dilator assembly 10 (i.e., the end portion of the dilator assembly 10 that contacts the soft tissue) when the dilator assembly 10 is in the contracted position and the expanded position, respectively. As shown, the outer diameter D2 of the dilator assembly 10 along the bottom end (i.e., along the axial bottom of the blades 60) is smaller in the contracted position (i.e., FIG. 7) and larger in the expanded positon (i.e., FIG. 8). For example, the outer diameter D2 along the blades 60 in the contracted position may be approximately 14.8 mm and in the expanded position may be approximately 33.0 mm.

To use the dilator assembly 10 and expand the dilator assembly 10 from the contracted position to the dilated position, the guide pin 26 is first inserted into the disc 12, as shown in FIG. 1. In particular, the guide pin 26 is inserted into a portion of the spine where the disc 12 and the adjacent vertebral bodies are shaped like a "hump." The rest of the dilator assembly 10 (while in the contracted position) is then slid over the guide pin 26 such that the guide pin 26 is positioned within the inner tube assembly 50. Accordingly, the guide pin 26 may be slidably and removably coupled to the inner tube assembly 50. The dilator assembly is stabilized manually in an axial fashion against the spine.

To expand the dilator assembly 10, the dilator assembly 10 functions similarly to a mechanism for opening an umbrella. In particular, by rotating the handle 30 (in a clockwise direction, for example), the handle 30 draws or pulls the outer tubular member 52 further into the handle 30 in a proximal direction (due to the threaded connection) while pushing or thrusting on a base (i.e., the top, T-shaped end including the shoulder 90) of the inner tubular member 54 in a distal direction through the thrust bearings 96 in the handle 30. In this motion, the handle 30 also applies a downward axial force on the inner tubular member 54 of the inner tube assembly 50 and moves the inner tubular member 54 and the outer tubular member 52 axially relative to each other. In particular, the outer tubular member 52 is moved upwardly relative to the inner tubular member 54.

Figure 11A:
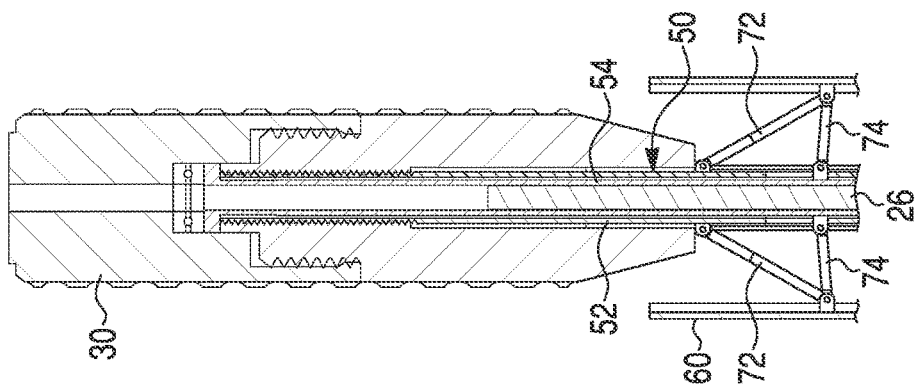
FIG. 11A is a close-up view of a portion of the dilator assembly of FIG. 1 in the contracted position.
Figure 11B:
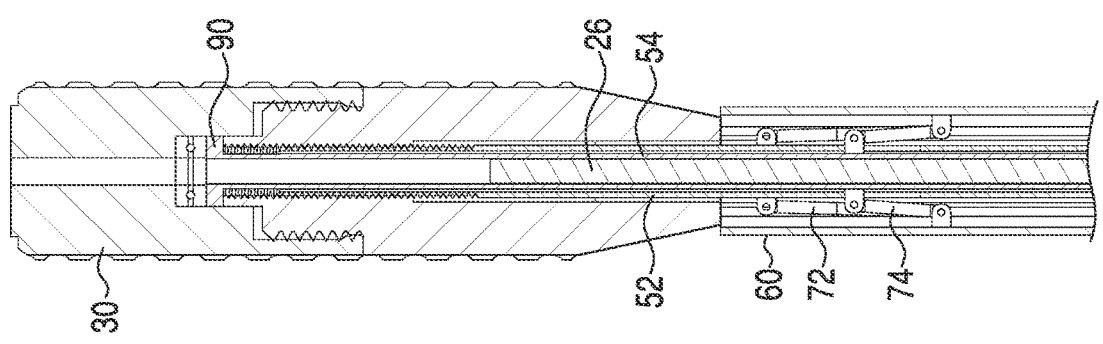
FIG. 11B is a close-up view of a portion of the dilator assembly of FIG. 1 in the expanded position.

As the handle 30 continues apply an axial downward force to the inner tubular member 54 and the outer tubular member 52 continues to move axially upwardly (relative to the inner tubular member 54), the outer tubular member 52 pulls the inner end of the upper links 72 (which are hingeably attached to the outer tubular member 52) upwardly, axially away from the inner end of the lower links 74 (which are hingeably attached to the inner tubular member 54), thereby further axially separating the respective inner ends of the links 72, 74 relative to the contracted position (as shown in FIGS. 11A-11B). As the links 72, 74 axially further separate from each other, the lower link 74 moves axially within and along the length of the slot 38 of the outer tubular member 52 (as shown in FIGS. 12A-12B).

By further axially separating the respective inner ends of the links 72, 74, the links 72, 74 (in particular the lower link 74) force the blades 60 to move radially outwardly due to the hinged attachment of the blades 60 to the inner tube assembly 50 via the links 70 (in particular the hinged attachment between the outer ends of the links 72, 74 to the blades 60). Additionally, the tapered portion 100 may engage the blades 60 as the outer tubular member 52 moves upward relative to the inner tubular member 54, further forcing the blades 60 to move radially outward. Since the blades 60 are attached to the inner tube assembly 50 (via the links 72, 74), the blades 60 are moved axially congruently with the inner tube assembly 50 until the blades 60 encounter and are axially stopped by the outer surface of the disc 12. Additionally, since the axial ends of the blades 60 directly abut and are pressed against the disc 12 and therefore cannot move axially downwardly any further, the blades 60 can only move or displace radially outwardly.

As the blades 60 move radially outwardly, the axial ends of the blades 60 slide along the disc 12 and the edges of the adjacent vertebral bodies 14, which radially outwardly pushes the surrounding soft tissue and creates a tubular cavity in the soft tissue. Once the dilator assembly is fully expanded in the expanded position, the surgeon can then access the disc 12 and/or place other retractors or instruments into the cavity and/or the disc 12.

According to one embodiment as shown in FIGS. 9A-9B, the dilator assembly 10 has a double inner tube assembly 50 (e.g., double-walled inner tubes that include the outer tubular member 52 and the inner tubular member 54) and double links 70 (i.e., links 70 that include the upper link 72 and the lower link 74 and are positioned in pairs, as described further herein). This arrangement improves the outward leverage force as the dilator assembly 10 moves between the contracted position and the extended position, thereby allowing the dilator assembly 10 to expand outwardly more powerfully. As a double inner tube assembly 50 the inner tube assembly 50 comprises an outer tubular member 52 and an inner tubular member 54 that is positioned radially within the outer tubular member 52. The outer tubular member 52 and the inner tubular member 54 may be movably attached to each other, as described further herein. By providing the double links 70, the dilator assembly 10 of FIGS. 9A-9B provides additional structural support. For example, this dilator assembly 10 (in particular the upper links 72) prevents the lower links 74 from moving axially upwardly past a perpendicular position, which prevents the entire dilator assembly 10 from moving past the expanded position (and into an upwardly collapsed position) while moving from the contracted position to the expanded position.

Both of the links 70 (in the pair of links) are attached and hingeably mounted directly to either to the inner tubular member 54 or the outer tubular member 52 of the double inner tube assembly 50. For example, the upper link 72 may be attached and hingeably mounted directly to the outer tubular member 52, and the lower link 74 may be attached and hingeably mounted directly to the inner tubular member 54 through the slot 38 in the outer tubular member 52. However, the dilator assembly 10 may have the opposite configuration or both the upper link 72 and the lower link 74 may be attached to the same inner tubular member 54 or outer tubular member 52. If one of the links 72 or 74 is hingeably mounted to the inner tubular member 54, the outer tubular member 52 may include a corresponding axially-extending slot 38 through and along which the link 72 or 74 extends (to attach to the inner tubular member 54) and can move.

In the embodiment of FIGS. 9A-9B, the handle 30 may be two pieces (e.g., the top portion 92 and the bottom portion 94) that are permanently threaded to each other after assembly. In the expanded position (and the contracted position), the guide pin 26 does not protrude from the top of the handle 30 and pushing is not required to move the dilator assembly 10 to the expanded position. By turning the handle 30, equal forces are imparted on each of the blades 60. Furthermore, all of the blades 60 are linked together and move in concert with each other. The dilator assembly 10 may optionally stay closed in the contracted position during insertion.

To use the dilator assembly of FIGS. 9A-9B, first, the patient is typically in a lateral position, but could alternatively be in a in a prone or oblique position. The guide pin 26 is then inserted retro-peritoneal so that the tip touches a segment of the spine. The rest of the dilator assembly (in the contracted position) slides down over the guide pin 26 (toward the spine) until distal ends of the blades 60 touch the spine. The handle 30 turns, thereby moving the dilator assembly from the contracted position to the expanded position. A plurality of (for example, four) retractor blades are inserted in between the blades 60. The dilator assembly is closed by turning the handle 30 in the opposite direction and is then withdrawn, leaving access to the site (which is exposed by the retractor blades that hold the site open). The guide pin 26 is then withdrawn.

Figure 10A:
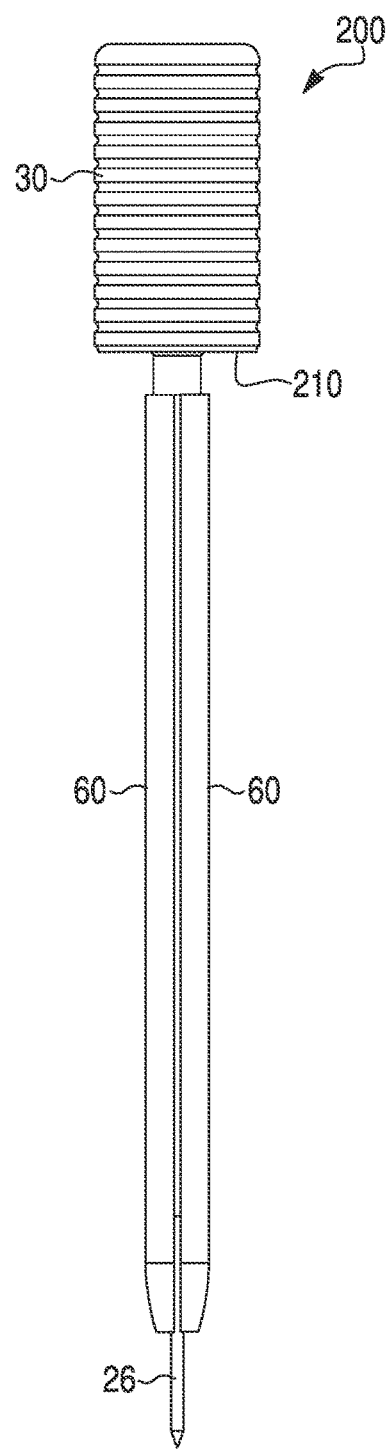
FIG. 10A is a side view of a dilator assembly according to another embodiment in a contracted position.
Figure 10B:
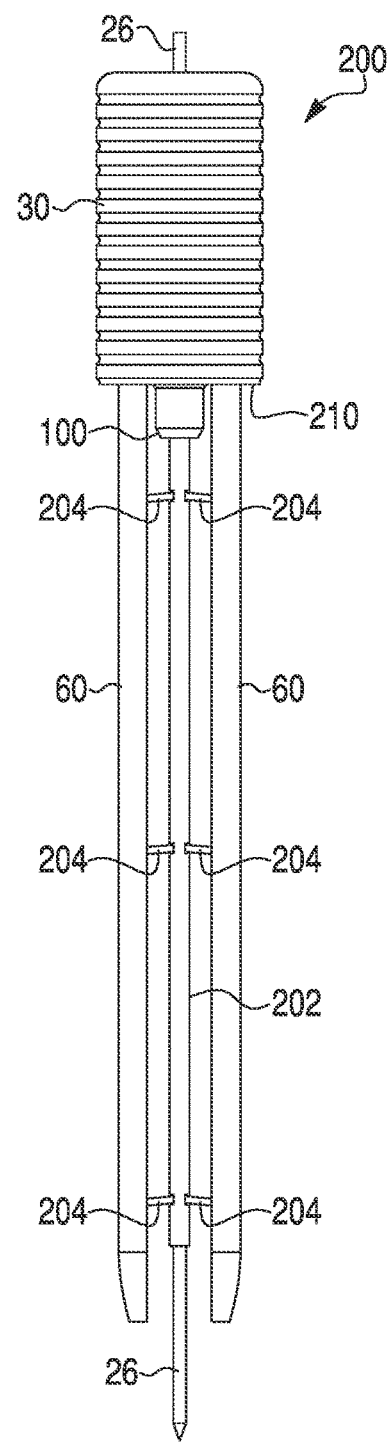
FIG. 10B is a side view of a dilator assembly of FIG. 10A in an expanded position.

Referring to FIGS. 10A-10B, a dilator assembly 200 is shown according to an exemplary embodiment. The dilator assembly 200 may be substantially similar to the dilator assembly 10 except as otherwise specified herein. The dilator assembly 200 has a single tubular member 202 and single links 204 (i.e., links that are not positioned in pairs). This arrangement still allows the dilator assembly 200 to include the same functionality as described further herein, while reducing the number of required parts and geometric complexity. Accordingly, the dilator assembly of FIGS. 10A-10B is simpler and easier to manufacture, costs less, and is smaller (e.g., radially smaller) in the contracted position (compared to the dilator assembly of FIGS. 9A-9B). The dilator assembly 200 may include any combination of a double inner tube assembly 50 or a single tubular member 202 and double links 70 or single links 204, according to the desired configuration.

In the embodiment of FIGS. 10A-10B, the handle 30 is detachable from the rest of the dilator assembly 200. In the expanded position, the guide pin 26 may protrude from the top of the handle 30 (as shown in FIG. 10B). The pushing force imparted on the vertebral body by the distal end of the blades 60 may be at a maximum force when in the contracted position. The blades 60 are independently attached to the inner tube assembly 50 and movable relative to each other. Accordingly, the blades 60 can independently move between the contracted and expanded positions if resistance is encountered during insertion. The blades 60 may each result in different depths (due to different insertion distances) within the created tubular cavity.

To use the dilator assembly of FIGS. 10A-10B, first, the patient is typically in a lateral position, but could alternatively be in a in a prone or oblique position, lying on their side. From the incision site, the tissues are manually separated, and the guide pin 26 (which may be 14 gauge or 2.11 millimeters) is guided to spine. The guide pin 26 is then inserted so that the tip just or partially penetrates the superficial annulus fibrosis or disc (which prevents the dilator assembly from sliding out of position during use). The dilator assembly 200 (in the contracted position) is slid down over the guide pin 26 until the distal ends of the blades 60 touch the vertebral body. The handle 30 slides down over the guide pin 26 until the handle 30 touches the proximal end of the inner tube assembly 50. The guide pin 26 may protrude through the top of handle 30. A protective cap may cover the protruding portion of the guide pin 26. The handle 30 is then pushed downwardly such that the blades 60 spread radially outwardly and until a flat portion or shoulder 210 of the handle 30 touches the proximal ends of the blades 60, thereby stopping any further dilation. A plurality of (for example, four) retractor blades may be fixed at the site, interdigitated between separated blades 60. The handle 30 may be removed for better access. The dilator assembly (including the guide pin 26) may be moved back to the contracted position and removed from the site, leaving access to the site (which is exposed by the retractor blades that hold the site open).

Referring to FIGS. 13A-15B, a dilator assembly 300 is shown according to another exemplary embodiment. The dilator assembly 300 may be substantially similar to the dilator assembly 200 except as otherwise specified herein. The dilator assembly 300 may comprise three blades 310 (instead of four blades 60, as described further herein) with an asymmetric configuration. This particular dilator assembly 300 may be used for posterior spine applications when accessing the spine for decompressions or screw placement.

As shown in FIGS. 15A-15B, the blades 60 may have an asymmetric design. For example, any combination of the blades 310 may have different arc lengths (and thus cover different amounts of the inner tube assembly 50). According to one embodiment, one of the three blades 310 (i.e., a blade 312) extends approximately 180° around the inner tube assembly 50, and the two other of the three blades 310 (i.e., blades 314) each extend approximately 90° around the tubular member 202. As shown in FIGS. 15A and 15B, the blades 314 are offset approximately 90° from one another, and the blades 314 are offset approximately 135° from the blade 312.

Figure 13A:
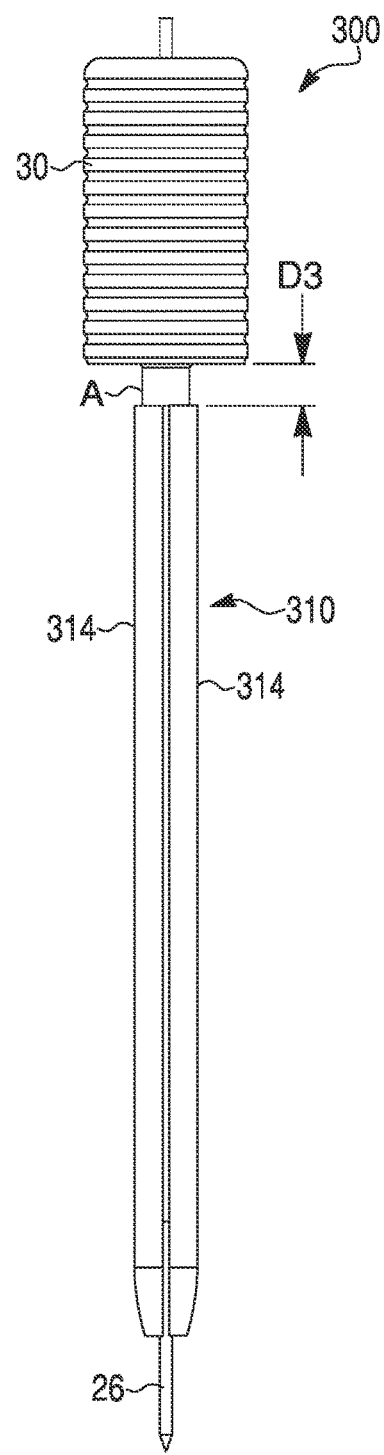
FIG. 13A is a side view of a dilator assembly according to one embodiment in the contracted position.
Figure 13B:
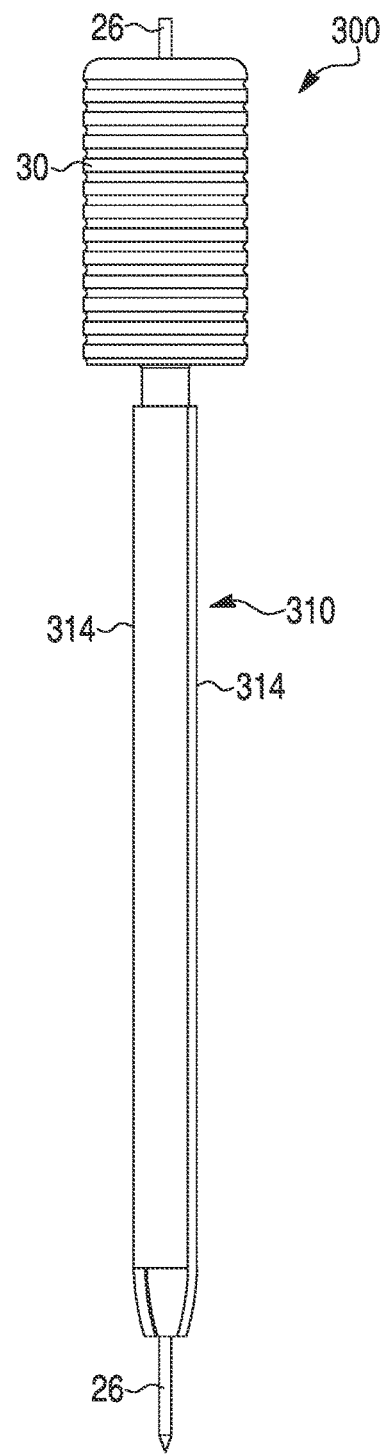
FIG. 13B is a side view of the dilator assembly of FIG. 13A, rotated approximately 15°.

As shown in FIGS. 13A and 14B, as the blades 310 move between the contracted position and the expanded position, the blades 310 move axially along the length of the entire dilator assembly 300. In particular, as the dilator assembly 300 moves from the contracted position to the expanded position, the blades 60 axially move in a direction toward the handle 30 (as the blades 310 move radially away from the tubular member 202). Similarly, as the dilator assembly 300 moves from the expanded position to the contracted position, the blades 310 axially move in a direction away from the handle 30 (as the blades 310 move radially toward from the tubular member 202). According to one embodiment, the distance D3 between the top of the blades 310 and the bottom of the handle 30 is approximately 9.09 mm in the contracted position and 0.00 mm in the expanded position.

In the contracted position, the distance D4 between the outer surfaces of the blades 310 (i.e., the outer diameter of a circle formed by the outer surfaces of the blades 310, taken along a cross-section that is perpendicular to the central axis of the dilator assembly 300) is approximately 13.34 mm. In the expanded position, this distance D2 is approximately 31.52 mm. According to various embodiments, however, the dilator assembly 300 may have a variety of different shapes along a cross-section that is taken perpendicular to the central axis of the dilator assembly 300, such as circular or oval. Accordingly, the blades 310 and/or the tubular member 202 may be shaped accordingly.

Each of the various implementations of the dilator assembly disclosed herein may have any of the aspects, features, components, and configurations of the other implementations, except where noted otherwise.

As utilized herein, the term "approximately" and similar terms are intended to have a broad meaning in harmony with the common and accepted usage by those of ordinary skill in the art to which the subject matter of this disclosure pertains. The term "approximately" as used herein refers to ±5% of the referenced measurement, position, or dimension. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the invention as recited in the appended claims.

The terms "coupled," "connected," "attached," and the like as used herein mean the joining of two members directly to one another. Such joining may be stationary (e.g., permanent) or moveable (e.g., removable or releasable).

References herein to the positions of elements (e.g., "top," "bottom," "above," "below," etc.) are merely used to describe the orientation of various elements in the FIGURES. It should be noted that the orientation of various elements may differ according to other exemplary implementations, and that such variations are intended to be encompassed by the present disclosure.

It is important to note that the construction and arrangement of the various exemplary implementations are illustrative only. Although only a few implementations have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. For example, the position of elements may be reversed or otherwise varied, and the nature or number of discrete elements or positions may be altered or varied. The order or sequence of any process or method steps may be varied or re-sequenced according to alternative implementations. Other substitutions, modifications, changes and omissions may also be made in the design, operating conditions and arrangement of the various exemplary implementations without departing from the scope of the present invention.

What is claimed is:

1. A dilator assembly, comprising:
   a blade;
   a tubular member defining a passage extending along a longitudinal axis;
   a guide needle received within the passage and configured to be inserted into a spine;
   a first link having a first end pivotally coupled to the tubular member and a second end pivotally coupled to the blade; and
   a second link having a first end pivotally coupled to the tubular member and a second end pivotally coupled to the blade.

2. The dilator assembly of claim 1, further comprising a handle coupled to an end of the tubular member, the handle including a tapered portion that is configured to engage the blade to force the blade away from the tubular member.

3. The dilator assembly of claim 1, wherein the blade is a first blade, the dilator assembly further comprising:
   a second blade;
   a third link coupled to the tubular member and the second blade; and
   a fourth link coupled to the tubular member and the second blade.

4. The dilator assembly of claim 3, wherein the tubular member is centered about the longitudinal axis, and wherein the first blade and the second blade are radially offset from one another about the longitudinal axis.

5. The dilator assembly of claim 1, wherein the guide needle is slidably coupled to the tubular member such that the guide needle is longitudinally translatable relative to the tubular member.

6. The dilator assembly of claim 1, wherein the guide needle includes a tapered tip configured to be inserted into the spine.

7. The dilator assembly of claim 1, wherein the guide needle is removably coupled to the tubular member.

8. The dilator assembly of claim 1, wherein the guide needle is removable from the tubular member by sliding the guide needle out of the passage.

9. The dilator assembly of claim 1, further comprising a handle coupled to an end of the tubular member, wherein the blade extends a first distance from the handle, wherein the guide needle extends a second distance from the handle, and wherein the second distance is greater than the first distance.

10. The dilator assembly of claim 1, wherein the guide needle is configured to be inserted into the spine without the blade penetrating soft tissue adjacent the spine.

11. A dilator assembly, comprising:
    a blade;
    a guide needle extending along a longitudinal axis;
    an inner tubular member extending along the longitudinal axis, the inner tubular member defining an aperture that receives the guide needle;
    an outer tubular member slidably coupled to the inner tubular member and configured to translate relative to the inner tubular member along the longitudinal axis, the outer tubular member defining a passage that is centered about the longitudinal axis and that receives the inner tubular member;
    a first link having a first end pivotally coupled to the inner tubular member and a second end pivotally coupled to the blade; and
    a second link having a first end pivotally coupled to the outer tubular member and a second end pivotally coupled to the blade,
    wherein the first link and the second link are configured to move the blade away from the inner tubular member and the outer tubular member in response to longitudinal movement of the outer tubular member relative to the inner tubular member.

12. The dilator assembly of claim 11, wherein the passage is a first passage, wherein the outer tubular member defines a second passage extending outward from the first passage, wherein the inner tubular member includes a protrusion extending into the second passage, and wherein the protrusion is pivotally coupled to the first end of the first link.

13. The dilator assembly of claim 11, wherein the blade is a first blade, the dilator assembly further comprising:
    a second blade coupled to the inner tubular member by a third link; and
    a third blade coupled to the inner tubular member by a fourth link,
    wherein the inner tubular member and the outer tubular member are centered about the longitudinal axis, and wherein the first blade, the second blade, and the third blade are configured to move radially outward relative to the longitudinal axis in response to longitudinal movement of the outer tubular member relative to the inner tubular member.

14. The dilator assembly of claim 13, further comprising a fourth blade coupled to the inner tubular member by a fifth link, wherein the first blade, the second blade, the third blade, and the fourth blade are configured to move radially outward relative to the longitudinal axis in response to longitudinal movement of the outer tubular member relative to the inner tubular member.

15. A dilator assembly, comprising:
a blade;
a first member extending along a longitudinal axis;
a second member slidably coupled to the first member and configured to translate relative to the first member along the longitudinal axis;
a first link having a first end pivotally coupled to the first member and a second end pivotally coupled to the blade; and
a second link having a first end pivotally coupled to the second member and a second end pivotally coupled to the blade,
wherein the first link and the second link are configured to move the blade away from the first member and the second member in response to longitudinal movement of the second member relative to the first member; and
wherein the first link and the second link are pivotally coupled to the blade at the same location such that the first link and the second link rotate relative to the blade about a common axis.

16. The dilator assembly of claim 15, further comprising a third link having a first end pivotally coupled to the first member and a second end pivotally coupled to the blade.

17. The dilator assembly of claim 16, further comprising a fourth link having a first end pivotally coupled to the second member and a second end pivotally coupled to the blade.

18. A dilator assembly, comprising:
a blade;
a first member extending along a longitudinal axis;
a handle coupled to an end portion of the first member;
a second member slidably coupled to the first member and configured to translate relative to the first member along the longitudinal axis;
a first link having a first end pivotally coupled to the first member and a second end pivotally coupled to the blade; and
a second link having a first end pivotally coupled to the second member and a second end pivotally coupled to the blade,
wherein the first link and the second link are configured to move the blade away from the first member and the second member in response to longitudinal movement of the second member relative to the first member; and
wherein the handle is rotatably coupled to the end portion of the first member and in threaded engagement with an end portion of the second member, wherein rotation of the handle relative to the first member causes longitudinal movement of the first member relative to the second member.

19. The dilator assembly of claim 18, wherein the end portion of the first member defines a shoulder, wherein the handle includes a first portion selectively coupled to a second portion, and wherein the shoulder is received between the first portion and the second portion of the handle.

20. The dilator assembly of claim 18, wherein the handle includes a tapered portion that is configured to engage the blade in response to movement of the second member toward the handle, forcing the blade away from the first member.

* * * * *